United States Patent [19]

Reinmüller

[11] Patent Number: 5,077,281

[45] Date of Patent: Dec. 31, 1991

[54] NOVEL USE OF TAUROLIN

[76] Inventor: Johannes Reinmüller, Erhardtstrasse 40, D - 7900 Ulm, Fed. Rep. of Germany

[21] Appl. No.: 55,624

[22] PCT Filed: Sep. 19, 1986

[86] PCT No.: PCT/EP86/00545

§ 371 Date: May 19, 1987

§ 102(e) Date: May 19, 1987

[87] PCT Pub. No.: WO87/01591

PCT Pub. Date: Mar. 26, 1987

[30] Foreign Application Priority Data

Sep. 20, 1985 [DE] Fed. Rep. of Germany ....... 3533612

[51] Int. Cl.$^5$ .................. A61K 31/725; A61K 31/54; A61K 31/35

[52] U.S. Cl. .................. 514/56; 514/222.5; 514/457; 514/822

[58] Field of Search ............ 514/222.5, 56, 457, 514/822

[56] References Cited

U.S. PATENT DOCUMENTS 4,337,251  6/1982  Pfiermann .................. 514/222.5
4,587,268  5/1986  Pfirrmann .................. 514/222.5

OTHER PUBLICATIONS

Stedman's Medical Dictionary 24th ed p. 25.
The Molecular and Cellular Biology of Wound Repair Clark et al, 1988 pp. 3-33.
R. W. Pfirrmann "A New Concept for Antimicrobial Chemotherapy of Surgical Infections, Introduction and Overview" pp. 3-23 in Taurolin published by W. L. Bruckner & R. W. Pfirrmann Verlag Urban and Schwazenberg, Munchen 1985.
Von C. Steinbach-Lebbin et al, "On the Pharmacokinectics of Taurolin" pp. 1542-1546, Arzneim.-Forsch./Drug Res. (II), Nr. 12 (1982).

Primary Examiner—Frederick E. Waddell
Assistant Examiner—Raymond J. Henley, III
Attorney, Agent, or Firm—Felfe & Lynch

[57] ABSTRACT

Taurolin compounds are used as blood coagulation-inhibiting agents and as abacterial inflammation-inhibiting agents. The outstanding coagulation-inhibiting action of taurolin is especially suitable for use in medical conditions requiring dialysis and for vascular protheses. These compounds can also be used together with other anti-coagulants such as coumarin or heparin.

15 Claims, No Drawings

NOVEL USE OF TAUROLIN

DESCRIPTION

It is known to counter a blood embolus formation (thrombosis) to a certain extent by administration of coagulation-inhibiting medicaments. Coagulation-inhibiting medicaments (anticoagulants) in the narrower sense delay or prevent the blood coagulation; to these medicaments belong heparin and the coumarins, such as e.g. Marcumar ® (3-(1-phenylpropyl)-4-hydroxycoumarin). In addition, there are also known so-called coagulation-inhibiting medicaments in the wider sense which are certain fibrinolytic and thrombolytic (i.e. fibrin- and blood embolus-dissolving) materials, such as e.g. streptokinase and urokinase, and inhibiting materials of the thrombocyte aggregation or of the prostaglandin synthesis, such as e.g. acetylsalicylic acid.

Taurolin is used in medicine as a good bactericidally-active substance. Taurolin has a low solubility in water (about 1%). Because of its very good bactericidal and other properties (no resistance against this substance known; apart from individually occurring slight local tissue irritation, other undesired side effects are not known), solutions of taurolin are used for bone lavage for the combating and treatment of bacterial osteolitis and bacterial suppurative peritonitis. Besides the very good bactericidal effectiveness, for taurolin is also known an inhibiting action on the formation of adhesions of the peritoneum after operative intervention into the abdominal cavity, as well as the suitability of taurolin for the neutralization of the endotoxin in the case of the so-called endotoxin shock; further medicinal fields of use have hitherto not been known for taurolin (cf. e.g. C. Steinbach-Lebbin et.al., Arzneimittelforschung/Drug Research 32 (II), No. 12 (1982), 1542–1546; W. Siegenthaler, Klinische Pathophysiologie, Georg Thieme Verlag, Stuttgart 1976).

It has now been found that, besides its known good bactericidal action, taurolin surprisingly also displays a coagulation-inhibiting action. Therefore, the subject of the present invention is the use of taurolin as blood coagulation-inhibiting agent, especially for the extracorporeal circulation, for example for plasmaphoresis, dialysis, blood lavage, oxygenators and for protheses in the vascular system.

The action according to the invention is surprising and also in "Taurolin", published by W. L. Bruckner and R. W. Pfirrmann, Verlag Urban und Schwarzenberg, Munchen 1985, it is expressly stated that taurolin does not influence the blood coagulation and displays no anti-phlogistic action.

Since the coagulation-inhibiting action of taurolin occurs not only in vivo but also in vitro, taurolin can, as mentioned, also be used for the coagulation inhibition in the extracorporeal circulation (e.g. in the case of heart operations or in the case of haemodialysis in the artificial kidney). The use of taurolin is thereby above all indicated in those cases in which the formation or entrainment of blood emboli in the vascular system (e.g. thrombosis, embolism) is to be prevented, thus in the first place in the case of heart infarct and in the case of vein thrombosis with the danger of a lung embolism, but also in the case of threatening blockage of blood vessels, in the case of blood vessel diseases and after injuries or operations for the prevention of the post-traumatic thromboses.

An undesired side effect of the known anti-coagulants, such as heparin or the coumarin derivatives, results, above all, from their desired coagulation-inhibiting and therefore, inter alia, blood flow-promoting actions. It can thereby, above all, result in hemorrhages in the gastro-intestinal tract (e.g. in the case of the so-called "quiet" gastric ulcer, in brain hemorrhages and in hemorrhages in the draining off urinary tract or in would hemorrhages during and after operations and after injuries. For the avoidance of such undesired phenomena, it is, therefore, important to monitor the remaining coagulatability of the blood during the administration by means of various coagulation tests, e.g. by the so-called "Quick test". In the case of an overdosing, hitherto the too strong action in the case of the coumarin derivatives must be reduced by high doses of coagulation factors and possibly also of vitamin K and the too strong action of heparin must be removed e.g. by neutralization with protamine.

It has now been ascertained that in the case of the use according to the invention of taurolin as coagulation-inhibiting agent, these disadvantages do not occur but, on the contrary, a sufficient blood coagulatability is always still maintained and, therefore, even in the case of an inadvertent false dosaging, the danger does not exist that a complete suppression of the blood coagulation takes place and thus dangerous hemorrhages could occur. Thus, e.g. it was found in vitro that in the case of the addition of taurolin to blood plasma (5 ml. of pooled plasma of various persons was mixed with increasing amounts up to max. 50 mg. taurolin, whereby the maximum dosage, i.e. thus 50 mg./5 ml., corresponds to a 1% solution, which simultaneously also corresponds to the solubility limit of taurolin), a corresponding reduction of the Quick value and an also corresponding prolongation of the PTT occurs and the blood coagulation is not completely suppressed as is the case e.g. under the same conditions in the case of the use of heparin. Therefore, in comparison with known anti-coagulants, the use of taurolin has the advantage that a sufficient blood coagulatability always still remains and, therefore, an overdosing is not possible.

In the case of vascular protheses, hitherto the thrombus formation on the surface was prevented either by binding of coagulation-inhibiting heparin in the inner walls of the protheses or recently increasingly by coating with physical plasmas. However, the action of these measures has been found to be very brief. For the long-term maintenance of the function of a vascular prothesis, one now aims for the formation of a so-called neointima on the inner walls of protheses. For the formation of a neointima, the synthetic resin surfaces of the lumen of the vascular prothesis (e.g. Dacron or Teflon) must woven velours-like and brought into contact with blood components; this best takes place before the implantation. After the implantation, there then takes place a deposition of white blood cells on the so pretreated surfaces. After a comparatively long contact with the blood, there was obtained the formation of a substantially complete endothelial layer on the velours surface. This artificially produced endothelial layer, which is called neointima, can prevent the undesired thrombi formation on the surface of the prothesis. However, this process possesses the disadvantage that it is very time-consuming and laborious. Furthermore, it is thereby necessary, up to the formation of a dependable neointima, additionally to administer systemic anti-coagulants for months and years, which involves the known risks.

In the case of the use of taurolin according to the invention as coagulation inhibitor, this disadvantage can be avoided, i.e. the time-consuming and laborious process for the prevention of the thrombi formation on the prothesis surface can thereby be overcome in a simple way in that one treats the surface with taurolin and then exposes directly to the blood stream. In this way, the result which one otherwise achieves by formation of the neointima is achieved practically immediately. Alternatively, one can also introduce the taurolin directly into the blood stream. This embodimental form is also unquestionable because the tauroli, in the case of the maximum possible dosaging in the blood, lowers the Quick value to a maximum of 20% and does not increase the PTT value above 60 seconds. These data correspond to the therapeutic values aimed for in the case of the treatment of heart infarct patients with Marcumar ®. This means that thus also in the case of the treatment of the heart infarct, the previously known anti-coagulants, such as e.g. Marcumar ® and heparin, can be replaced by taurolin, whereby, in addition, one can also avoid the disadvantages involved with the previously known anti-coagulants, such as especially the danger of hemorrhages.

The dosaging and manner of application of taurolin depends upon the field of use and the therapeutic aim in general according to the guidelines known for the known anti-coagulants, such as e.g. Marcumar ® and heparin, whereby the most suitable values for the particular individual case, modes of administration and measures are easy to determine by orientating tests, such as e.g. the measurement of the reduction of the Quick value. As taurolin, in the scope of the invention are understood compounds of the general formula

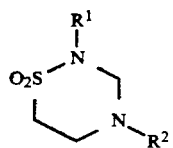

wherein $R^1$ signifies a hydrogen with 1 to 6 carbon atoms and $R^2$ a hydrogen atom, an alkyl radical with 1 to 6 carbon atoms or a radical according to the general formula

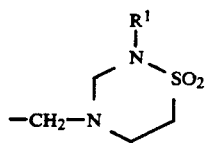

wherein $R^1$ possesses the given meanings.

4,4'-Methylene-bis-(tetrahydro-2H-1,2,4-thiadiazine-1,1-dioxide) is preferred. A similar coagulation-inhibiting action, in part in weakened form, can also be shown by the compounds standing in equilibrium in an aqueous solution of taurolin (e.g. 2H-1,2,4-thiadiazine-1,1-dioxide and especially its 4-hydroxymethyl derivative and the ring fission products standing in equilibrium in the case of heating, such as e.g. 1-hydroxymethylamino-2-sulphamoylethane and 1-amino-2-sulphamoylethane), as well as the taurolin metabolites (cf. C. Steinbach-Lebbin et.al., Arzneimittelforschung/ 5 Drug Research 32 (II), No. 12 (1982) 1542-1546). Therefore, above and in the following, by taurolin is also to be understood these decomposition products and metabolites.

As dialysis materials and vascular protheses, there can be used all materials hitherto known and described in the literature (cf. e.g. Artificial Organs, Vol. 5 (Suppl.) 1981 507; Trans. Am. Soc. Artif. Intern. Organs, Vol. XXV (1979) 280; Vol. XXVII (1981) 396, 499, 511 and 648; Vol. XXVIII (1982) 459 and 478; Vol. XXIX (1983) 200).

The administration can, as a rule, take place in the usual manner for anti-coagulants, thus e.g. intravenously, intraperitoneally, perorally or as infusion. In comparison with heparin, the taurolin used according to the invention further possesses the advantage that it maintains the action, with equally rapid commencement, long and uniformly and taurolin can also be administered orally; the use previously necessary in many cases (e.g. in the treatment of a heart infarct) of the combination of an initial heparin injection and subsequent oral administration of a coumarin derivative, the action of which admittedly commences delayed but can be administered in oral form, is thereby not necessary. A solution of taurolin in water is preferably used.

For the use according to the invention as coagulation-inhibiting agent, the taurolin can be administered as sole component or also together with other components. The form of administration (pharmaceutical composition) can contain conventional additive materials, such as conventional pharmaceutical confectioning and/or dilution agents, and possibly also further active materials insofar as these show no undesired side effects with the other components and are suitable for the assistance of the therapy; in particular, in some cases it can also be expedient to use the taurolin together with known anti-coagulants, such as e.g. heparin and/or coumarin derivatives, such as Marcumar ®, e.g. simultaneously (in the same form of administration) or also one after the other. A reduction of the dose of the known anti-coagulants and thus of their known risks in use is hereby also possible.

It has also been found that the single contact with taurolin with an artificial surface, such as e.g. of a synthetic resin or metal surface, continuously effectively prevents the deposition of blood coagula on the artificial surface in vivo, i.e. after an implantation or a temporary introduction of an object of the synthetic material into an organism through which blood flows. Therefore, this coagulation action can serve for the use of the taurolin for the treatment of surfaces of medical apparatus which are temporarily introduced into the blood stream, such as e.g. vein catheters (which, untreated, tend to blockage due to blood coagula which again represents a breeding place for bacteria, whereby the danger of a sepsis is brought about). The treatment of the apparatus can be carried out e.g. with an aqueous taurolin solution, especially a 1% aqueous taurolin solution. By means of an intermittent rinsing of vascular catheters, it is, in this way e.g. possible to prevent the coagula formation on the catheter tips.

The manner of action of taurolin on the blood coagulation system differs fundamentally from that of the previously known coagulation-inhibiting agents. Coumarin derivatives act by reduction of the rate cf synthesis of coagulation factors—as vitamin K antagonists; therefore, their action takes place delayed, i.e. in dependence upon the half life time of the coagulation factors which amount to between 20 and 100 hours. Heparin acts by activation of antithrombin III which, in turn, functions as inhibitor of the serine proteases of the coagulation system; furthermore, it is bound to the cell surfaces of the cells on the walls of the blood vessels—the endothelial cells—and to various co-factors of the coagulation. In contradistinction thereto, taurolin inhibits dependent upon concentration and thereby readily controlably the function of antithrombin III. Taurolin can thereby also be used as antidote (counter-agent) in the case of heparin over-dosings with the advantage that, after the use of taurolin, due to the taurolin a coagulation-inhibiting action still remains.

On the basis of its surprising novel coagulation-inhibiting action, there furthermore also comes into question the use of taurolin as antidote (counter-agent) when the coagulation system has been activated by other blood coagulation-effective substances, such as e.g. snake venom (cf. e.g. "Methods in Enzymology, Vol. XLV, "Proteolytic Enzymes", Part B, 1976, Academic Press, New York/San Francisco/London).

How the coagulation-inhibiting action of the taurolin comes about could not yet be fully elucidated. However, a marked direct action of the taurolin on the Factor XII of the coagulation system was ascertained; this is of especial interest because the activated Factor XII brings about the activation of the kallikrein/kinine system, of the fibrinolysis system and of the complement system. Since inflammatory reactions of the vascular connective tissue are brought about especially via the kallikrein/kinine system but also via the complement system, the taurolin has, therefore, also an inflammation-inhibiting action. From this result the following medicinal uses (indications) for taurolin: non-bacterial inflammations of the bones, of the cartilage and of the soft parts, e.g. arthritis, arthroses, rheumatoid diseases in the chronic and acute stage; inflammations of glandular organs and of the gastro-intestinal tract, e.g. the non-bacterial inflammation of glandular organs; allergic inflammations, e.g. toxic nephritis; chronic inflammations which can form around implanted foreign materials without the co-action of bacteria. Thus, taurolin can be used e.g. for the slowing down or suppression of the foreign body reaction of the organism. For this purpose, the active material taurolin can be introduced e.g. into the interior of the foreign material in order then, after implantation, to emerge into the organism or into the surrounding tissue and there manifest its intended action.

Therefore, the subject of the present invention is also the use of taurolin as inflammation-inhibiting agent, especially in the scope of the above-mentioned indications.

The following Examples explain the invention in more detail without limiting it thereto.

EXAMPLE 1

Foils of cellulose acetate were treated with a 15 aqueous solution of taurolin (period of action 30 minutes at 37° C.) and subsequently brought into contact with fresh blood (period of action 30 minutes at 37° C.). After removal of the blood and rinsing off of the foil surface with physiological common salt solution, no fibrin fibre deposition on the surface could be ascertained by electron raster photographs, whereas one was ascertained in the case of surfaces not pretreated with taurolin solution but otherwise the same.

A cellulose acetate foil which was first brought into contact with a taurolin/blood plasma mixture (taurolin 1% dissolved in the plasma) subsequently also showed no blood coagulation or fibrin deposition on the wall when it is thereafter rinsed with physiological common salt solution and then incubated with fresh blood from healthy donors for 30 minutes at 37° C.

It was also found that, quite generally, the surface of synthetic materials which are implanted in an organism become thromboresistant by contact with taurolin and maintains this effect when the taurolin has already been removed from the surface. From this it is recognized that the contact according to the invention of taurolin with an artificial surface effectively continuously prevents the deposition of blood coagula on the artificial surface in vivo, i.e. after implantation of the device of synthetic material in an organism with blood flow-through.

EXAMPLE 2

Samples of, in each case, 5 ml. of a pooled plasma of various experimental persons were mixed with increasing amounts of taurolin, namely, with amounts of 0 (1), 10 (2), 20 (3), 30 (4), 40 (5) and 50 (6) mg. of taurolin/5 ml. plasma (the figures given in brackets give the sample numbers).

The Quick test and the PTT test was carried out for the samples 1 to 6 and the following results (30 minutes) obtained (Table 1):

|  | sample No. | | | | | |
| --- | --- | --- | --- | --- | --- | --- |
|  | 1 | 2 | 3 | 4 | 5 | 6 |
| Quick test (%) | 92 | 65 | 53 | 44 | 39 | 35 |
| PTT (in sec.) | 34.1 | 38.0 | 43.0 | 48.8 | 55.9 | 61.8 |

Furthermore, in the case of samples 1 to 6, for the various coagulation factors (plasma factors), there was determined the reduction of the values by the taurolin addition (according to the methods of factor analysis as are stated by the manufacturers of corresponding test systems, e.g. of Behringwerke AG, Marburg or American Hospital Supply Deutschland GmbH, Munchen).

The results obtained are summarized in Table 2:

TABLE 2

| sample No. | coagulation factor | | | | | | | |
| --- | --- | --- | --- | --- | --- | --- | --- | --- |
|  | II | V | VII | X | IX | XI | XII | VIII |
| 1 | 108% | 164% | 94% | 82% | 321% | 312% | 185% | 121% |
| 2 | 96% | 121% | 79% | 75% | 153% | 301% | 177% | 48% |
| 3 | 87% | 110% | 74% | 65% | 81% | 197% | 77% | 21% |
| 4 | 90% | 92% | 74% | 56% | 63% | 140% | 64% | 13% |
| 5 | 75% | 81% | 77% | 53% | 65% | 83% | 55% | 6% |
| 6 | 74% | 79% | 73% | 50% | 68% | 47% | 61% | 6% |

The values in Table 2 show clearly that all investigated blood factors are reduced by taurolin (initial value is the absolute value in percent given for the untreated sample No. 1) but that in no case does a reduction to 0% take place.

The results contained in Example 2 show that, under the conditions employed, the blood coagulation is not completely suppressed by the taurolin, whereas this is the case, e.g. in the case of replacement of taurolin by heparin under otherwise the same conditions. From this can be seen that the use of taurolin according to the invention, in the case of its use as coagulation inhibitor, is less questionable than the previously known coagulation inhibitors because, due to the incomplete suppression of the blood coagulation even in the case of unintended false dosaging (over-dosaging), the danger does not exist of the complete suppression of the blood coagulation and thus of a hemorrhage.

I claim:

1. A composition in a pharmaceutically effective amount for preventing blood coagulation comprising a taurolin compound of the formula

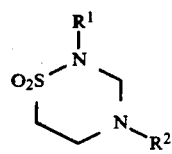

wherein $R^1$ is H or a $C_1$-$C_6$ alkyl and $R^2$ is H, a $C_1$-$C_6$ alkyl or a group of the formula:

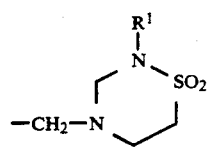

wherein $R^1$ is H or a $C_1$-$C_6$ alkyl, and
heparin or an anti-coagulant coumarin derivative consisting of 3-(1-phenylpropyl)-4-hydroxycoumarin wherein the compounds are present in an amount effective to lower the Quick value to a maximum of 20% and wherein the PTT value does not increase above 60 seconds in a patient.

2. A reagent for preventing blood coagulation comprising a
pharmaceutically effective amount of at least one taurolin compound of the formula

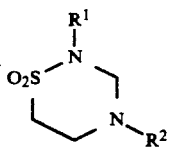

wherein $R^1$ is H or a $C_1$-$C_6$ alkyl, $R^2$ is H, $C_1$-$C_6$ alkyl or a group of the formula

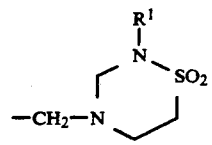

wherein $R^1$ is H or a $C_1$-$C_6$ alkyl, and
heparin or a coumarin derivative consisting of 3-(1-phenylpropyl)-4-hydroxycoumarin wherein the compounds are present in an amount effective to lower the Quick value to a maximum of 20% and wherein the PTT value does not increase above 60 sec. in a patient.

3. A method of inhibiting blood coagulation in or near prosthetic device after said device has been inserted in a patient which comprises administering a taurolin compound to the prosthetic device in a pharmaceutically effective amount sufficient to inhibit blood coagulation in or about said device after insertion f placement in or on the patient in need of the device and wherein the taurolin compound is of the formula:

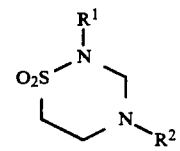

wherein $R^1$ is H or a 1-6 carbon alkyl group and $R^2$ is H, a 1-6 carbon alkyl group or a group of the general formula:

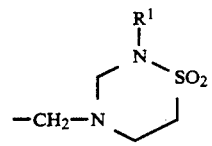

wherein $R^1$ is H or a 1-6 carbon alkyl group.

4. Method of claim 3 comprising administering said taurolin compound to the prophetic device by administration into a patient's extracorporeal circulation.

5. Method of claim 3 comprising administering said taurolin compound to a prosthetic device consisting of a vascular prothesis inserted in said afflicted subject.

6. Method of claim 3 wherein said subject is afflicted with at least one condition selected from the group consisting of myocardial infarct, vein thrombosis, blood vessel blockage, blood vessel diseases and after injuries or operation for the prevention of post-traumatic thrombosis.

7. A method according to claim 3 wherein said taurolin compound is 4,4'-methylene-bs-(tetrahydro-2H,1,2,4-thiadiazine-1,1-doxide).

8. A method for inhibiting blood coagulation in or near a prosthetic device wherein said device is inserted into the extracorporeal circulation of a patient which comprises
administering a taurolin compound to the prosthetic device in a pharmaceutically effective amount sufficient to inhibit blood coagulation in or about said device together with or after insertion or placement into the extracorporeal circulation of the patient and wherein the taurolin compound is of the formula

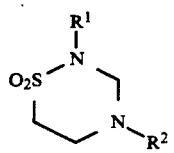

wherein $R^1$ is H or a 1-6 carbon alkyl group and $R^2$ is H, a 1-6 carbon alkyl group or a group of the general formula:

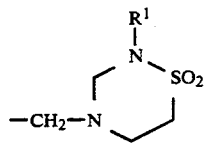

wherein R¹ is H or a 1-6 carbon alkyl group.

9. A method for inhibiting coagulation of blood caused by vascular prosthesis or extracorporeal devices in a patient which comprises:

treating the surface of the prosthesis or device with an effective blood coagulation inhibiting amount of a taurolin compound of the formula

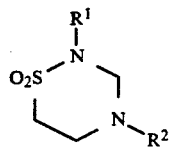

wherein R¹ is H or a 1-6 carbon alkyl group and R² is H, a 1-6 carbon alkyl group or a group of the general formula:

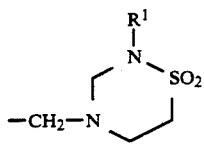

wherein R¹ is H or a 1-6 carbon alkyl group.

10. The method of claim 9 further comprising administering said tauroling compound to the blood circulation in an amount effective to inhibit blood coagulation.

11. Method of any one of claim 3, 8 or 9 further comprising inhibiting blood coagulation by administering the taurolin compound together with another anti-coagulant comprising a coumarin derivative consisting of 3-(1-phenylpropyl-4-hydroxycoumarin or heparin wherein the anti-coagulant compounds are present in a pharmaceutically effective amount.

12. Method for preventing blood coagulation in the use of vascular catheter and prosthesis in a patient which comprises:

administering to the circulation a pharmaceutically effective amount of a taurolin compound selected from the group consisting of 4-4-Methylene-bos-(tetrahydro 2-H-1,2,4-thiadiazine-1,1-dioxide, 1-hydroxymethylamino-2-sulphamoylethane, 1-amino-2-sulphamoylethane or a 4-hydroxymethyl derivative thereof, and 2H-1,2,4-thiadiazine-1,1-dioxide or a 4-hydroxymethyl derivative thereof to inhibit blood coagulation.

13. Method for inhibiting blood coagulation in the use of vascular prostheses in a patient which comprises:

administering to the circulation a pharmaceutically effective amount of a taurolin compound 4-4'-Methylene-bis-(tetrahydro-2H-1,2,3-thiadiazine-1,1-dioxide) to inhibit blood coagulation.

14. A method for inhibiting blood coagulation in a patient having a medical condition requiring blood coagulation-inhibition which comprises administering to the circulation of a patient in need of said blood coagulation-inhibition treatment up to a 1% solution of a taurolin compound selected from the group consisting of 4-4-Methylene-bis-(tetrahydro-2H-1,2,4-thiadiazine-1-amino-2-sulphamyl-ethane, 2H-1,2,4-thiadiazine-1,1-dioxide and a 4-hydroxymethyl derivative of 2H-1,2,4-thiadiazine-1,1-dioxide to inhibit blood coagulation.

15. Method for combating an overdoes of a blood-coagulation active agent comprising administering to a patient in need thereof an effective amount o a taurolin compound of the formula:

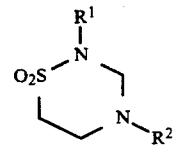

wherein R¹ is H or a C₁–C₆ alkyl and R² is H a C₁–C₆ alkyl or a group of the formula

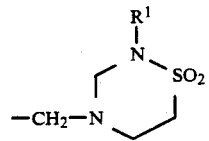

wherein R¹ is H or a C₁–C₆ alkyl.

* * * * *

UNITED STATES PATENT AND TRADEMARK OFFICE
CERTIFICATE OF CORRECTION

PATENT NO. : 5,077,281
DATED : December 31, 1991
INVENTOR(S) : Johannes Reinmuller It is certified that error appears in the above-identified patent and that said Letters Patent is hereby corrected as shown below:

| | |
|---|---|
| Col. 3, line 45: | after "a hydrogen" insert -- atom or an alkyl radical --. |
| Col. 3, line 67: | after "Arzneimittelforschung/" delete "5". |
| Col. 5, line 66: | change "15" to -- 1% --. |
| Col. 8, line 8: | change "insertion f" to -- insertion of --. |
| Col. 8, line 44: | change "4,4'-methylene-bs-(tetrahydro-" to -- 4,4'-methylene-bis-(tetrahydro- --. |
| Col. 9, line 38: | change "tauroling" to -- taurolin --. |
| Col. 9, line 48: | change "catheter" to -- catheters --. |
| Col. 10, line 3: | change "4-4-Methylene-bos-" to -- 4-4'-Methylene-bis- --. |
| Col. 10, line 22: | change "4-4-Methylene" to --4-4'-Methylene --. |
| Col. 10, line 23: | change "1-amino-2-sulphamyl-ethane," to -- 1-amino-2-sulphamoyl-ethane --. |

UNITED STATES PATENT AND TRADEMARK OFFICE
CERTIFICATE OF CORRECTION

PATENT NO. : 5,077,281
DATED : December 31, 1991
INVENTOR(S) : Johannes Reinmuller It is certified that error appears in the above-identified patent and that said Letters Patent is hereby corrected as shown below:

Col. 10, line 26:  change "overdoes" to -- overdose --.

Signed and Sealed this

Nineteenth Day of October, 1993

Attest:

BRUCE LEHMAN

Attesting Officer    Commissioner of Patents and Trademarks